United States Patent [19]

Ettipio

[11] 4,100,621
[45] Jul. 18, 1978

[54] ARTIFICIAL BREAST AND NIGHTGOWN INCORPORATING SAME

[76] Inventor: Marion Carol Ettipio, 70 Alma Ave., Buffalo, N.Y. 14215

[21] Appl. No.: 730,090

[22] Filed: Oct. 7, 1976

Related U.S. Application Data

[63] Continuation-in-part of Ser. No. 603,542, Aug. 11, 1975, abandoned.

[51] Int. Cl.$^2$ .............................................. A41D 9/00
[52] U.S. Cl. ................................... 2/114; 2/DIG. 6; 128/456; 128/481
[58] Field of Search ............... 128/450, 452, 456, 478, 128/479, 480, 481, 505; 3/36; 2/114, DIG. 6

[56] References Cited

U.S. PATENT DOCUMENTS

| | | | |
|---|---|---|---|
| 2,624,049 | 1/1953 | Granne | 2/114 |
| 3,161,200 | 12/1964 | Brickman | 128/479 X |
| 3,221,748 | 12/1965 | Glasser | 128/480 |
| 3,348,241 | 10/1967 | Dodds | 128/478 X |
| 3,401,407 | 9/1968 | Pittman | 3/36 |
| 3,878,568 | 4/1975 | Connelly | 3/36 |

FOREIGN PATENT DOCUMENTS

| | | | |
|---|---|---|---|
| 616,522 | 3/1961 | Canada | 2/DIG. 6 |

OTHER PUBLICATIONS

"Self-Adhering Nylon Tapes," *Journal of American Medical Association*, 10-1958, vol. 168, No. 7.

*Primary Examiner*—Werner H. Schroeder
*Assistant Examiner*—Moshe I. Cohen
*Attorney, Agent, or Firm*—Raymond F. Kramer

[57] ABSTRACT

An artificial breast or mastectomy prosthesis is a light weight substantially breast-shaped pad having hook type fastening means at a plurality of locations about the periphery of the pad, which are fastenable to mating pile attachment means on the inside of the bosom area of a nightgown and are readily removable therefrom, when desired. More particularly, the artificial breast is of substantially triangular outline shape, when viewed from the front thereof, with hook tape fastening means at each corner and extending away from the triangle and with pile attachment means, ready for fastening to a nightgown, removably held to the hook tape fastening means. Specific pad structures are also described, as are nightgowns with pile attachment means and artificial breasts of this invention attached thereto, and a method of removably attaching the described artificial breast or mastectomy prosthesis to the inside of a nightgown.

3 Claims, 8 Drawing Figures

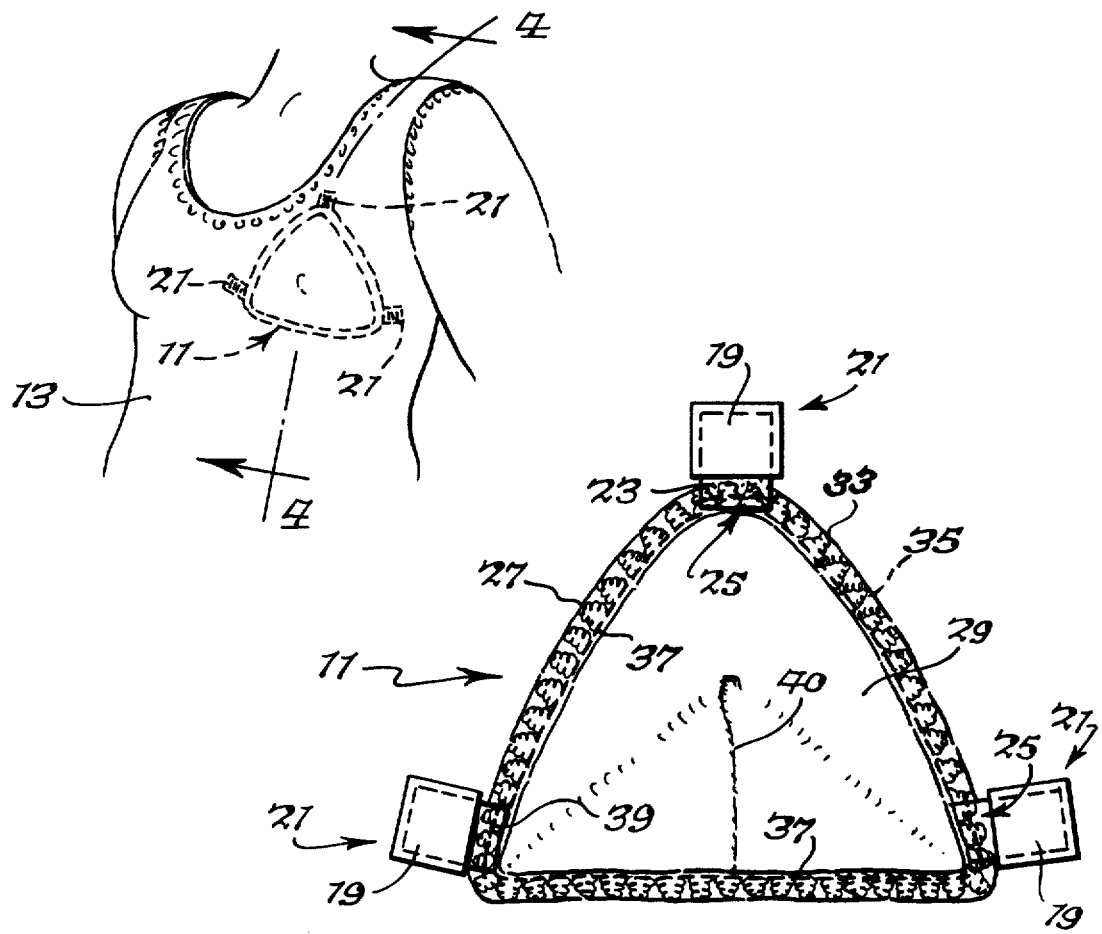
Fig. 1.
Fig. 2.
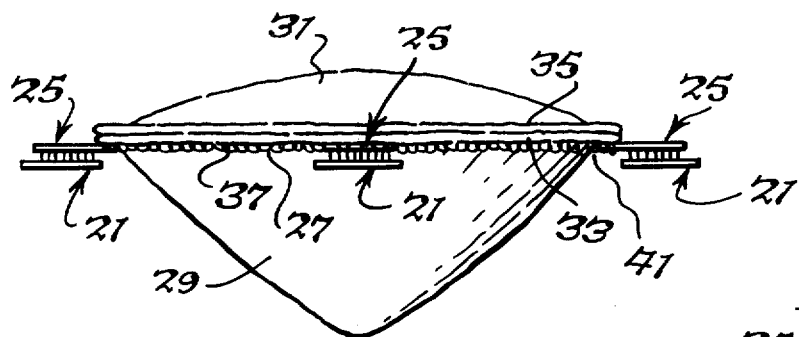
Fig. 3.
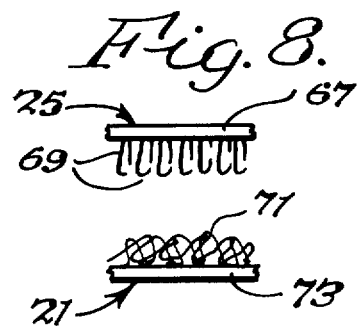
Fig. 8.

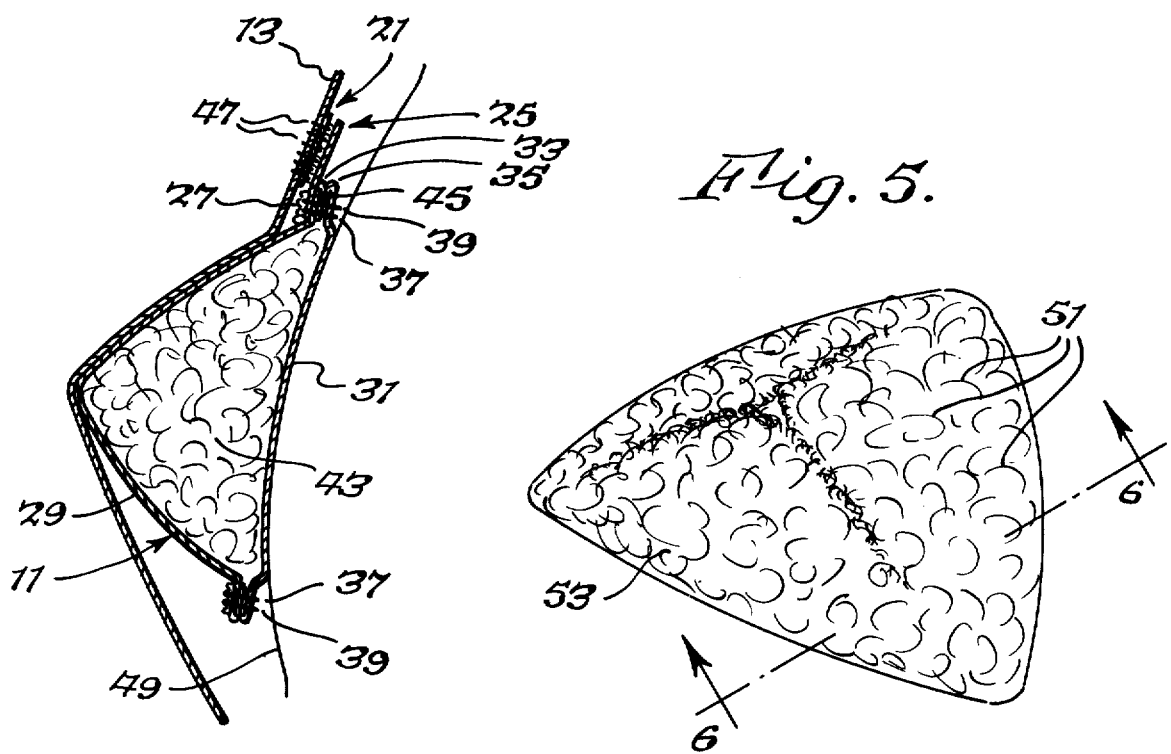
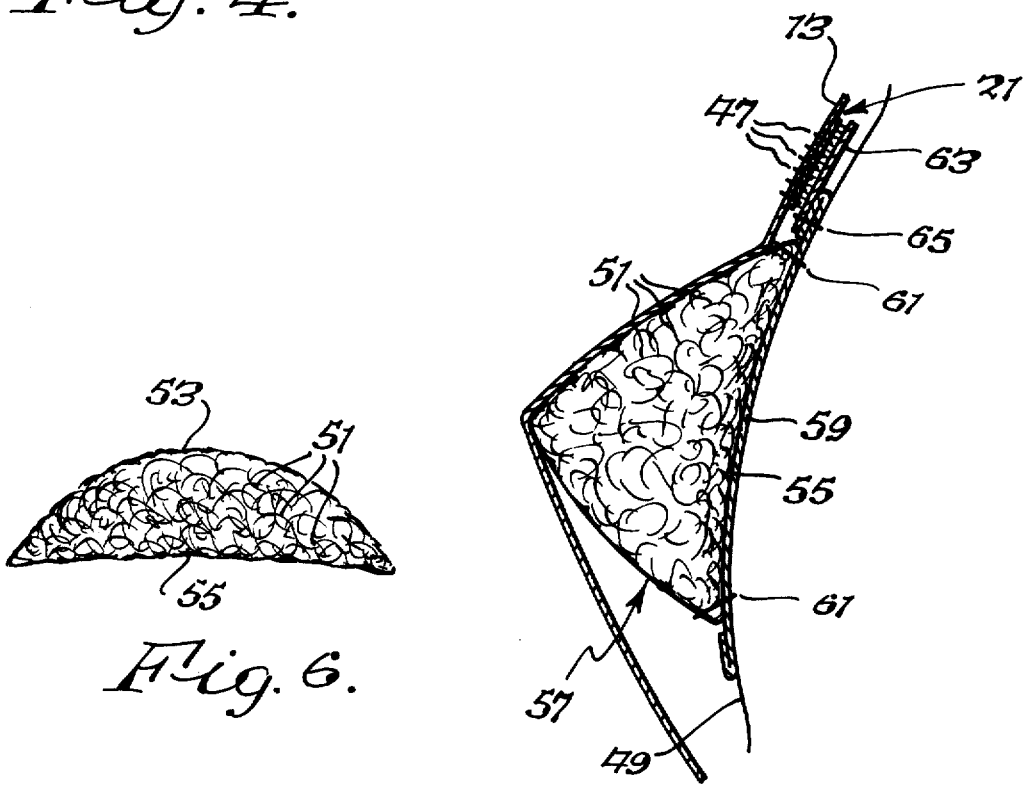

ARTIFICIAL BREAST AND NIGHTGOWN INCORPORATING SAME

This application is a continuation-in-part of my application, Ser. No. 603,542, for Mastectomy Bra-ette, filed Aug. 11, 1975, now abandoned.

This invention relates to an artificial breast or mastectomy prosthesis. More particularly, it relates to such an article which is fastenable to the inside of a nightgown or other such sleepwear item so as to make such gown hang naturally and to conceal the absence of a breast of the wearer. The invention also relates to the nightgown incorporating such artificial breast and to a method for applying the artificial breast to the nightgown so that it is adequately held thereto but is readily removable therefrom when desired.

Women who have undergone mastectomies will usually wear some type of prosthetic device, such as a special brassiere, so as to maintain a normal body shape. This is done to conceal the effect of the mastectomy, to make clothing fit better, to make the woman feel and appear more feminine and for psychological reasons. Similarly, women with undeveloped breasts may use padded brassieres. Special prosthetic brassieres are known in the prior art, as illustrated by U.S. Pat. No. 3,498,297, padded brassieres for flat-chested girls and women are well known. Especially with respect to the prosthetic brassieres, although such devices may be satisfactory for daytime wear, when worn in bed they tend to move upwardly and if tight enough not to move, they tend to be binding and thereby inhibit relaxation at night. As a result, to avoid the discomfort of the brassiere, especially when worn for a long time, and to prevent undesirable movement upward thereof when the wearer is lying down, the brassiere will often be removed. Of course, this results in a noticeable change in the woman's profile and the fitting of her nightgown and the resulting appearance is unsatisfactory and unacceptable to many women. Accordingly, it has been suggested to insert breast-form prostheses into interior pockets of a certain type of lounge wear. However, such pockets may be conspicuous, are not readily removable from garments to which they are attached and usually will be sewn to the garment when it is manufactured, because the wearer will not be as readily able to position them for best appearance as will be a knowledgeable manufacturer. This may be due mostly to the way the artificial breast will lie rather loosely in the pocket or may be because the pocket is difficult to hold in proper position on the nightgown for sewing into place. In addition to employing pockets for positioning such prostheses one may also utilize ties, buttons, snaps and zippers for holding the prosthesis in place against the nightgown but, as mentioned in U.S. Pat. No. 3,348,241, such may result in uncomfortable protrusions that could irritate sensitive areas near the site of a breast amputation.

It is an object of the present invention to produce an artificial breast especially suitable for attachment to sleepwear, such as a nightgown, on the inside thereof, to satisfactorily shape the sleepwear and give it the appearance of covering a natural breast. Another object is to have such a prosthetic device which is readily attachable to the sleepwear and removable from it to facilitate washing and to allow the user to employ the prosthetic device or not, as desired, with a particular nightgown. A further object is to manufacture such a product which may readily be used with any of a variety of nightgowns or similar sleepwear, with easy application of relatively inconspicuous attaching means onto the sleepwear interior. Still further objects of the invention will be apparent from this specification, including the drawing.

In accordance with the present invention an artificial breast or mastectomy prosthesis comprises a light weight substantially breast-shaped pad having hook type fastening means at a plurality of locations about the periphery thereof with the hooks extending forwardly, as viewed by a wearer of the artificial breast, so as to be readily affixable to mating pile attachment means on the inside of the bosom area of a nightgown and removable therefrom. More specifically stated, such a mastectomy prosthetic article, for attachment to the inside of a nightgown, comprises a light weight substantially breast-shaped pad of substantially equilateral triangular outline shape when viewed from the front thereof, with a lower side of the triangle being substantially horizontal and with the other two upper sides being rounded, with the pad being of rounded substantially conical shape when viewed from a side, and being composed of a substantially conically shaped front wall, fibrous shaping material sufficient to hold the front wall in desired breast shape and a convexly arcing back wall fastened to the front wall about the sides thereof and retaining the shaping material in the pad, a hook tape held to the upper corner of the pad and extending substantially vertically and away from the pad, hook tapes held to each of the lower corners of the pad and extending substantially horizontally and away from the pad, with the hooks of the hook tapes being on the sides of such tapes facing the nightgown when the article is attached to the nightgown and with the tapes being outside the triangular outline of the pad, and with each of the hook tapes having a corresponding pile tape affixed thereoto, which pile tapes are each of greater areas than the corresponding hook tapes and extend beyond each of the hook tapes at three sides thereof to facilitate joinder of the pile tapes to a nightgown and to facilitate temporary holding of the pile tapes to the nightgown during removal of the article from the nightgown during permanent positioning of the pile tapes thereon. Also, within the invention are a nightgown with the described article removably affixed to the inside of the bosom part thereof and a method of removably applying such article to the nightgown.

In the drawing:

FIG. 1 is a perspective view of a part of the upper body of a woman clothed in a nightgown to which a single artificial breast of this invention is attached;

FIG. 2 is a front elevational view of such artificial breast, showing pile tapes attached to corresponding hook tapes on the prosthesis;

FIG. 3 is a top plan view of the article of FIG. 2;

FIG. 4 is a sectional view along plane 4—4 of FIG. 1, showing the conforming of the nightgown to the prosthetic device and the prosthetic device to the body of the wearer;

FIG. 5 is a perspective view of a pad portion of a prosthetic article of this invention wherein fibrous stuffing material is fused or otherwise joined together at the surfaces thereof facing the nightgown, without an enclosing cloth cover;

FIG. 6 is a sectional view along plane 6—6 of FIG. 5;

FIG. 7 is a partial central vertical sectional view of the article of FIGS. 5 and 6 removably fastened to a nightgown and in position against the wearer's body; and FIG. 8 is a partial sectional view of corresponding hook and pile tapes, such as those used on the prosthetic article of this invention to fasten it to the gown, in opposed position, before being brought together into readily removable attachment.

In FIG. 1 an artificial breast or mastectomy prosthesis 11 is shown in use position between the body of a woman who has had her left breast amputated and a nightgown 13 that she is wearing. As shown, attachment of article 11 to nightgown 13 is by means of three flexible hook tape fasteners on the article and three corresponding mating pile attachment means 21, with the latter attachment means being fastened to the inside of the nightgown in the bosom area thereof covering the site of the amputation.

In FIG. 2 prosthetic article 11 is shown as supplied, with the reverse ("smooth" or tape) sides 19 of pile attachment means 21 facing the viewer and covering most of the hooking side 23 of the hook tape fastening means 25. To avoid visual confusion with decorative lace edging 27 the actual hooks on the "active" surface of hook tape fastening means 25 are not shown in FIG. 2. However, enlargements of such hooks and mating pile means are shown in FIG. 8. It will be noted that the areas of the pile attachment means at each of the corners of the prosthetic article are greater than those of the corresponding parts of the hook fastening means so that in each case there is an overlap of the pile tape over the hook tape, which, as will be seen later, facilitates joining of the pile means to the nightgown and gives a degree of adjustment of the position of the artificial breast on the nightgown, with good holding attachment of the hook tapes to the pile tapes. The lace edging 27 is sewn or otherwise suitably fastened to the cloth of the front wall 29 and the back wall 31 at turned under edges 33 and 35, respectively, as by stitches 37. The hook tapes 25 are similarly sewn in place to such edges by stitches 39 passing through both such walls and edges. The breast shape of the prosthetic article, indicated by shading lines, is obtained by cutting a generally squarish piece of cloth, with rounded sides and corners, so that a corner thereof is removed, together with the cloth extending from points half-way along sides adjacent to the corner to approximately the center of the modified square, and sewing the cut edges together interiorly along seam 40, resulting in the shape indicated.

In FIG. 3 the rounded, substantially conical shape of the invented article is shown, defined by the cloth of front wall 29 and the slightly convex shape of the back wall is also illustrated, defined by the cloth of back wall 31. Lace 27 is stitched to the flange or edge of the front wall at 41, thereby aiding in the production of such edge section. As indicated in FIG. 2, attachment pile tape 21 is of greater area and extends beyond the corresponding section of hook tape 25.

FIG. 4 illustrates the details of stitchings, stuffing, structure and fitting of the prosthetic article and its relation to the covering nightgown. Article 11, comprising front and back walls 29 and 31, respectively, and stuffed with fibrous shaping material 43, has the walls thereof stitched together at 37 about the periphery thereof, thereby containing the stuffing and having it shape the article. It will be noted that at the edges or flanges 33 and 35 the cloths of the front and back walls are turned in to double thicknesses and the internal two sides are sewn together by stitches 45 about the periphery of such edges, which stitches are concealed from external view. Stitches 37, which hold lace 27 to the cloth of the front wall 29 at edge 33 thereof, also help to produce such a flange. Hook tape means 25 are held to front and back wall members 29 and 31 at edge 33 by stitches 39 and corresponding and mating pile tape fastening means 21 are sewn to nightgown 13 by stitches 47. The light weight artificial breast 11 has the back wall 31 thereof readily conform to the shape of the breast portion of the body of the wearer of the article, indicated by numeral 49, due to any force applied by nightgown 13 and due to the weight of the article. Thus, the shape readily conforms to the contacting body portion and is comfortable and non-irritating because of its light weight and soft, smooth surface.

In FIGS. 5 and 6 a modification of the breast-shaped pad portion of the present structure is illustrated with the fibrous stuffing or shaping material, indicated by numeral 51, having been held in desired shape and then heat treated to produce a permeable or perforate skin 53 over it, which is strong enough to hold the exterior of the mass of fibers in a permeable or preferably, perforate film form, thereby, in effect, replacing front wall member 29 of FIGS. 2–4. Instead of fusion sealing of the thermoplastic fibrous material together at the front face or wall thereof, this may also be accomplished by employment of adhesives, cements, solvents or other means for forming a confining but permeable or perforate surface on fibers 51. While, as illustrated in FIG. 6, back wall 55 is also fused or adhered together it is not necessary that this be done, although when both the front and back walls are fused together in a desired shape they may be more readily converted to final desired form, which form is shown in FIG. 7.

FIG. 7 corresponds to FIG. 4 but instead of employing cloths to define the front and back walls of the prosthetic article such cloth is utilized only at the back wall, to make certain that the area of the article in contact with the sensitive skin at the excised breast area will not be uncomfortable or irritating to the wearer. Thus, in FIG. 7 artificial breast 57 has cloth back wall 59 stitched to it through back wall 55 thereof by stitches 61 (other fastenings can be used) and hook tape 63 is sewn to such backing member by stitching 65. Pile tape 21 is sewn to nightgown 13 by stitches 47, in the same manner as illustrated in FIG. 4. In neither FIG. 4 nor FIG. 7 are the lower hook and pile fastening means illustrated although their positions are also as shown in FIGS. 1–3.

In FIG. 8 parts of conventional hook tape 25 and pile tape 21 are illustrated in opposing form so that if brought together the hooks will engage the pile in removably holding relationship. The hook tape comprises backing or tape portion 67 and hooks 69 and the pile part comprises pile 71 and tape 73, in both cases the hooks or piles being firmly joined to the appropriate tape. Although not illustrated, other VELCRO ® and Scotchmate ® type fasteners may also be utilized and some of these will be mentioned later.

The artificial breast illustrated in FIGS. 2–4, is of substantially triangular outline shape when viewed from the front thereof and is of rounded, substantially conical shape when viewed from the side thereof. It includes a light weight, substantially breast-shaped pad with hook type fastening means thereon at a plurality of locations about the periphery thereof, with the hooks extending forwardly, as viewed by a wearer of the prosthesis, so as to be readily affixable to mating pile attachment means on the inside of the bosom area of a nightgown or similar sleepwear item, with the hooks and the attached pad being readily removable from the pile and the nightgown to which the pile may be attached. The pad may be made of any suitable material but preferably will be of such smooth, soft materials as are normally used for the manufacture of brassieres, e.g., polyesters, polyester-cotton blends, cotton, nylons, acetates, acrylics and various other blends thereof. Although instead of a closely woven cloth for the walls a gauze or knit type may be used, or even non-woven cloths or perforated films, normally a woven cloth will be employed and the weave thereof should be such that the shaping material or stuffing in the pad will not tend to escape therefrom. Of course, when the shaping fibers are fused together at the surfaces thereof or otherwise held in desired position, as illustrated in FIGS. 5–7, larger weave openings may be acceptable.

The shaping fibers or filaments employed as a stuffing inside the pad will normally resemble conventional absorbent cotton and such may sometimes be used but because of its tendency to mat and to dry slowly after being washed it is highly preferable that polyester fibers or similar preferably equivalent synthetic polymeric plastic be employed instead. Such fibers are usually of a diameter less than 0.1 mm., e.g., 0.005 to 0.05 mm. The thread employed to sew the pad portion together and to sew onto it the lace and hook type fastening means may be any suitable one but it should be compatible with the other components, especially the cloth front and back portions of the product and if any of the materials employed tend to shrink, they should be pre-shrunk so as to avoid bunching of the stitches or lace due to uneven shrinkages (or stretchings). Thus, while in one embodiment of the invention it is preferred to employ a 100% nylon cloth for the front wall and a 100% acetate cloth for the back, with 100% polyester stuffing, it is often more preferable to utilize all polyester fabrics, stuffing, thread and lace.

The pads of the invention may be made in various sizes, as is normal for such prosthetic devices and for brassieres, but in all such cases they will be light in weight, as will be the finished products. For example, a single mastectomy prosthesis, sometimes called a mastectomy braette, as in my parent application, which has been abandoned, will usually weigh from 10 to 40 grams, preferably from 12 to 30 grams. Of this total weight the stuffing will usually be from 10 to 50%, e.g., 15 to 35%, which weight is usually sufficient to maintain the desired shape of the article despite extensive use and periodic washings.

The hook and pile fastening means are any such suitable products but usually commercial products, such as those sold under the trademarks VELCRO and Scotchmate, will be used. However, any suitable such means which satisfactorily holds the artificial breast to the sleepwear product and yet allows ready release thereof in the normal "Velcro" release manner may be employed, providing that the surface of the "pile" structure (or the hook structure, if possible) is smooth and non-irritating. Among patents describing "hook and pile" fasteners (the term is used in this specification to describe such type of fasteners broadly in appropriate instances, not being limited specifically to hook and pile components only) are U.S. Pat. Nos. 2,717,437; 3,000,384; 3,009,235; 3,076,244; 3,130,111; 3,147,528; 3,154,837; 3,192,589; 3,387,345; and 3,900,652. Such fasteners are often made of nylon but also can be made of various materials, in whole or in part, for specific situations, including polyesters, acrylics, acetates, cotton and cotton-synthetic blends. The only strict requirements are that the "hook" members should be sufficiently firm to grip the pile members and sufficiently resilient to return to initial position after release from the pile and the pile members should be sufficiently strong so as not to be excessively broken or permanently distorted upon removal of the hooks therefrom. Usually the hooks and piles are joined to backing members, which have been designated as tapes herein (such term is also employed for the completed hooking and pile means). Such backing members may be made of various materials but nylons and polyesters are preferred.

The structure of the artificial breast that has been found to be best for the present application is one wherein the prosthesis, viewed from the front thereof, is of generally triangular shape and most preferably the triangle is substantially equilateral, with a side thereof being substantially horizontal when the article is in position on a nightgown. The upper sides are preferably rounded. Although hook tape fastening means may be located on other parts of the prosthesis it is very highly preferable that three such units be employed and that their locations be at the three corners of the article, with the means at the upper corner extending substantially vertically and the means at the lower corners extending substantially horizontally in a vertical plane, all said fastening means extending away from the body of the prosthesis. Such locations provide maximum support to hold the artificial breast properly in place against the nightgown and better resist various strains to which the attaching means may be subjected. Also, positioning of the pile means onto the nightgown for permanent fastening thereto is greatly facilitated by having the attaching means visible to the wearer during such positioning and also by having it extend beyond the attached hook means.

To manufacture the prosthetic articles of this invention one cuts the desired patterns for the front and back walls and sews together the front wall portions along seam 40 (FIG. 2). Then the edges of two of the sides of the triangle, preferably the rounded upper sides, are sewn together with "internal" stitching and, if desired, a portion of the third side may be similarly sewn, so long as an opening is left for insertion of the shaping fibrous material. The attached walls are then turned inside out to desired final position and are stuffed with the requisite amount of polyester fiber, after which the stitching may be completed externally. Next, the hook tapes may be sewn in place onto the cloth of the front wall, with the hooks pointing forwardly. After that the lace or other decorative material, if employed, may be stitched on, forming a flange or border about the prosthesis and furnishing another barrier against accidental removal of any of the fibrous shaping material.

When the pad of FIGS. 5–7 is utilized the procedure is similar but the pad should be oriented first before insertion. To manufacture the pad one may need only to place the desired amount of fibrous stuffing material in a mold or other suitable shaping device and heat seal (if thermoplastic) or cement the external surfaces thereof so that after such sealing is complete the fibers will retain a specific desired shape. Heat sealing may be along the edges of the pad only if the fibers are long enough but preferably it is effected along such edges, at least those that face forwardly, and the forward wall of the pad, that which faces the nightgown. Such can be accomplished by pressing the shaping fibers against the heated wall of a mold, to which release agent has been previously applied. Whether heat sealing a fibrous polymeric plastic pad face or adhering the fibers together by solvent or adhesive treatment of a surface thereof, it is highly desirable to maintain such surface liquid permeable and preferably perforate, so that at least 30%, e.g., 40 to 70%, of the surface is void, allowing easy drainage or expulsion of liquid therefrom and allowing air circulation therethrough. When the back wall of the pad is also similarly heat-, solvent- or adhesive-treated, similar surface voids should be provided and in some cases no such treatment should be effected. While light weight open cell polymeric plastic foams, such as elastomeric polyurethane foams, may be employed in place of the polyester fiber filler of this invention, either between cloth walls or in replacement of the entire described pad, and may have the fastening means attached directly or indirectly thereto, usually such products will not be as comfortable, cool, wear-resistant and generally satisfactory as those previously described, based on polyester fiber.

Because the present prosthesis is removably attachable to items of sleepwear and can be individually fitted to a plurality of such items it may be supplied with pile (or nap) tape portions (overlapping the hook portions is preferred) for fastening in desired position onto the nightgown. Thus, as illustrated in FIGS. 1-3 (and with the upper fastening means shown in FIGS. 4 and 7), each hook tape has a pile tape temporarily fastened to it and each pile tape is made to be fastened in desired position on the appropriate portion of a sleepwear item. Since the prosthesis can be used on a plurality of such sleepwear items extra pile tape means may be supplied. For example, while three hook tapes are joined to the prosthesis and three other pile tapes are removably joined to them, one to each, from 0 to 10 times that many, e.g., 1 to 5 times that many pile tapes may also be supplied with the prosthesis for application to different nightgowns so that the single prosthesis may be used with any of such nightgowns. In each case, due to the easy method of application of this invention it may be separately and specifically fitted for best results. The various "extra" pile tapes may be separately supplied or may be in a single piece or in a lesser number of pieces than finally made, to be cut to length and desired shape.

To apply the artificial breast or mastectomy prosthesis to an item of sleepwear the prospective wearer fits the artificial breast into place, while wearing the sleepwear, and readily bastes, pins, fastens with double sided tape or otherwise locates the pile tape portions to the inside of the nightgown. The pile tapes are then readily separated from the hook tapes and the prosthesis is removed and the pile tapes are sewn or otherwise permanently fastened to the nightgown at desired positions. After the pile tapes are sewn into place it is a simple matter to position the prosthesis whenever it is desired to wear it with the particular nightgown. It is readily removable and the pile tapes, with pile side facing the wearer, will not be irritating to her. The pile material will usually be of a fineness about like that of the polyester stuffing for the product and the pile or nap will be from 1 to 3 mm. thick, e.g., 1.5 to 2.5 mm., with an area of about 1 to 10 square millimeters, e.g., 3 to 6 sq. mm., to form a flexible pad which is non-irritating against the skin of the chest. Preferably such pad will extend 0.2 to 0.8 mm., e.g., 0.4 mm. past the hook tape to provide more cushioning, easier temporary fastening to the nightgown, as by stitching, during and/or after fitting thereof, and a desired degree of adjustability in the position of the prosthesis.

The advantages of the invention are many. The product is inexpensive, attractive, light weight, easy to apply and remove and, although the prosthesis is not designed to accurately duplicate a human breast, it does make the nightgown look as if it is covering a breast. Washing of the artificial breast is easily effected without removing the shaping fiber from the interior thereof but if desired, any such stuffing may be removed by leaving open a portion of the stitching or other sealing means around the border of the triangular article, preferably at the bottom thereof. In such a case the opening should be big enough so that the stuffing can be removed when desired but will not fall out of the prosthesis during normal use. If desired, such opening may be closable by means of matching hook and pile VELCRO or Scotchmate fasteners joining the interiors of the front and back walls together along the side thereof. Of course, because the filling material may be removable, it can be separately laundered for faster drying but with polyester or other suitable synthetic polymeric fibers, which do not absorb water to any significant extent, drying is readily effected even without removal of the filler. Because the prosthesis is light weight, soft and comfortable, the wearer can lie on it without feeling any discomfort, as might have been felt with other fastening means being employed and similarly, even without the prosthesis in place the wearer can lie on the corresponding portion of her nightgown without irritation, due to the soft padding effect of the pile fastening means.

Although preferred embodiments of the invention have been described various modifications of these may also be employed. Thus, the present description has been of the use of a single prosthesis but two may also be used, as in the case of double mastectomies. While different shapes may be employed for each breast this is normally not necessary, the illustrated prosthesis being useful for placement on the nightgown in either the right or left breast position. In the manufacture of the prosthesis stitching is the preferred method of joinders but various other methods may be utilized for holding front and back article walls together, for joining the hook tapes to the prosthesis and for joining the pile tapes to the nightgown, such as cementing, heat sealing, solvent fusion, etc. In some cases it may be desirable to make the fastening tapes of different shapes, such as circular, triangular, elliptical or of parts of such shapes and they may also be re-located. Sometimes, as when a nightgown already having a pile or nap thereon is being worn the device of this invention may be applied without previously fastening the pile tapes to nightgown but this is not preferred as there may be a tendency for the gown material to become roughened at the points of affixations of the hook tapes. Decorative lace has been shown on the illustrated article but may be omitted therefrom. Of course, flesh-colored materials are preferably employed for all visible portions of the prosthesis, including the front wall of the article and the back of the pile tape, especially for occasions when such are being employed with sheer nightgowns. Alternatively, the various parts of the present invention may, to the extent possible, be made transparent, with the tapes, hooks and piles also being as transparent as possible. However, the hooks will normally be at least 0.05 mm. long, from base to top, preferably 0.07 to 1.5 mm. long and of a thickness of at least 0.2 mm., preferably 0.3 to 0.5 mm. While the depth of the pile is not critical, it should match that of the hooks so as to allow close fastening between corresponding sections of these parts. Further descriptions of the hook and pile means of this invention are in the previously mentioned patents, all of which are hereby incorporated by reference.

The invention has been described with respect to various embodiments and illustrations thereof but is not to be considered to be limited to them because it is evident that one of skill in the art with the present specification before him will be able to utilize substitutes and equivalents without departing from the spirit of the invention.

What is claimed is:

1. A mastectomy prosthetic article for attachment to the inside of a nightgown comprising a light weight substantially breast-shaped pad of substantially equilateral triangular outline shape when viewed from the front thereof, with a lower side of the triangle being substantially horizontal and with the other two upper sides being rounded, with the pad being of rounded substantially conical shape when viewed from a side, and being composed of a substantially conically shaped front wall, fibrous shaping material sufficient to hold the front wall in desired breast shape and a convexly arcing back wall fastened to the front wall about the sides thereof and retaining the shaping material in the pad, a hook tape held to the upper corner of the pad and extending substantially vertically and away from the pad, hook tapes held to each of the lower corners of the pad and extending substantially horizontally and away from the pad, with the hooks of the hook tapes being on the sides of such tapes facing the nightgown when the article is attached to the nightgown and with the tapes being outside the triangular outline of the pad, and with each of the hook tapes having a corresponding pile tape affixed thereto, which pile tapes are each of greater areas than the corresponding hook tapes and extend beyond each of the hook tapes at three sides thereof to facilitate joinder of the pile tapes to a nightgown and to facilitate temporary holding of the pile tapes to the nightgown during removal of the article from the nightgown during permanent positioning of the pile tapes thereon.

2. A nightgown suitable for fastening thereto of a mastectomy prosthetic article which is a light weight substantially breast-shaped pad of substantially equilateral triangular outline shape when viewed from the front thereof, with a lower side of the triangle being substantially horizontal and with the other two upper sides being rounded, with the pad being of rounded substantially conical shape when viewed from a side, and being composed of a substantially conically shaped front wall, fibrous shaping material sufficient to hold the front wall in desired breast shape and a convexly arcing back wall fastened to the front wall about the sides thereof and retaining the shaping material in the pad, a hook tape held to the upper corner of the pad and extending substantially vertically and away from the pad and hook tapes held to each of the lower corners of the pad and extending substantially horizontally and away from the pad, with the hooks of the hook tapes being on the sides of such tapes facing the nightgown when the article is attached to the nightgown and with the tapes being outside the triangular outline of the pad which comprises pile tapes permanently fastened on the inside of a bosom area of the nightgown and adapted to have the hook tapes of the mastectomy prosthetic article fastened to them to hold such article in place on the inside of the nightgown, while pile tapes are of areas greater than those of the hook tapes and extend beyond the edges of such hook tapes so as to facilitate adjustable fitting of the prosthetic article to the nightgown.

3. A method of removably fastening to the inside of a nightgown a mastectomy prosthetic article comprising a light weight substantially breast-shaped pad having hook tapes in a plurality of locations at the periphery thereof, with the tapes being outside the triangular outline of the pad, with hooks extending forwardly, as viewed by a wearer of such article and nightgown so as to be readily affixable to mating pile tapes on the inside of the nightgown and removable therefrom, which pile tapes are of greater areas than the corresponding hook tapes so that at least a portion of each thereof extends beyond the hook tape fastening means, which comprises fitting the mastectomy prosthesis article in desired position against the inside of the nightgown with pile tapes held to the hook tapes and with sides of said pile tapes extending beyond sides of the hook tapes, impermanently affixing the pile tapes at such extending sides in desired fitted position on the nightgown, removing the hook tapes from the pile tapes and removing the prosthetic article from the nightgown while holding the pile tapes in position on the nightgown, permanently fastening the pile tapes to the nightgown and placing the prosthetic article in position against the nightgown with the hook tapes matching the pile tapes and pressing such tapes together.

* * * * *